(12) United States Patent
Kuth et al.

(10) Patent No.: US 6,542,768 B1
(45) Date of Patent: Apr. 1, 2003

(54) SIGNAL PICKUP OR SIGNAL GENERATOR FOR A MAGNETIC RESONANCE TOMOGRAPHY DEVICE

(75) Inventors: Rainer Kuth, Herzogenaurach (DE); Arne Reykowski, Erlangen (DE); Hubertus Fischer, Bamberg (DE); Jianmin Wang, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 250 days.

(21) Appl. No.: 09/624,383

(22) Filed: Jul. 27, 2000

(30) Foreign Application Priority Data

Jul. 30, 1999 (DE) .......................... 199 35 915

(51) Int. Cl.⁷ .................. G01V 3/00; G01R 33/20; H01J 1/00
(52) U.S. Cl. .................. 600/411; 600/410; 324/319
(58) Field of Search ................ 600/411, 410, 600/418, 421, 425; 324/322, 319, 314, 309, 307

(56) References Cited

U.S. PATENT DOCUMENTS

| 4,614,999 A | * | 9/1986 | Onodera et al. ........... 363/28 |
| 4,616,181 A | * | 10/1986 | Kemner et al. ........... 324/309 |
| 5,473,252 A | | 12/1995 | Renz et al. |
| 5,663,648 A | * | 9/1997 | Chapman et al. .......... 324/318 |
| 5,684,402 A | * | 11/1997 | Rohan et al. ............. 324/318 |

FOREIGN PATENT DOCUMENTS

| JP | 3-183321 | * | 8/1991 | ............. H02J/1/00 |
| JP | 4-217 | * | 1/1992 | ............. H02J/1/00 |
| WO | WO 98/03887 | * | 1/1998 | ............. G01V 3/00 |

OTHER PUBLICATIONS

"Doppelschicht eröffnet neue Dimensionen," Raible et al., Components 6/98, pp. 28–29.

1994 Catalog from Bürklin, p.D2.

* cited by examiner

*Primary Examiner*—Hieu T. Vo
(74) *Attorney, Agent, or Firm*—Schiff Hardin & Waite

(57) ABSTRACT

The energy supply device for a signal pickup or signal generator for use in or at a magnetic resonance tomography device has a double layer capacitor of high capacitance and high power density. Charging of the double layer capacitor can occur via an integrated charging coil that derives charging energy from the high-frequency and/or gradient fields of the device.

13 Claims, 3 Drawing Sheets

SIGNAL PICKUP OR SIGNAL GENERATOR FOR A MAGNETIC RESONANCE TOMOGRAPHY DEVICE

BACKGROUND OF THE INVENTION

1. Field of the Invention

The present invention concerns a signal pickup or signal generator of the type having an energy supply device for use in or at a magnetic resonance tomography device.

2. Description of the Prior Art

Magnetic resonance tomography is a known modality for acquiring images of the internal organs of a live examination subject. A basic field magnet produces a static, optimally homogeneous basic magnet field in the magnitude of one Tesla. Quickly switched gradient fields that are produced by gradient coils are superimposed on this basic magnetic field during the acquisition of magnetic resonance images. A high-frequency transmission antenna emits high-frequency pulses into the examination subject for triggering magnetic resonance signals. A high-frequency reception antennas acquire the generated magnetic resonance signals on the basis of which magnetic resonance images are prepared.

In addition to antennas referred to as whole body high-frequency antennas, that generally are firmly connected to the magnetic resonance tomography device, there are also antennas referred to as local high-frequency reception antennas that pickup the magnetic resonance signals from a relatively small body area and are positioned at the appropriate point depending on the area to be imaged of the examination subject. Also, the local high-frequency reception antennas are connected to the magnetic resonance tomography device via a flexible lead, in order to conduct the received signals to processing stages and/or to supply the local antenna with auxiliary energy.

A high-frequency antenna connected via a lead is moved, for example, together with the patient lying on a movable examination table, into the center of the basic field magnet. During this moving process, the lead can be pinched or loops can form. A high-frequency reception antenna is known with a lead that has at least one plug connection, e.g. at the interface between lead and the magnetic resonance tomography device. Such a plug connection is subject to general wear and tear and can be easily soiled, for example, by body fluids of a patient and thereby impaired in function. Moreover, disturbing skin-effect (surface) waves on the lead can lead to an undesired high power density and induction heating of tissues (bordering the lead) of the examination subject. To avoid this, skin-effect wave barriers are provided in the lead.

The aforesaid disadvantages have motivated the development of lead-less, local high-frequency reception antennas. For the energy supply, these lead-less high-frequency reception antennas have accumulators or batteries. In order to forestall impairments to the magnetic resonance image quality, such accumulators or batteries cannot contain any ferromagnetic components. A lead-less, local high-frequency reception antenna that has an amplifier unit is also known from the German patent publication German PS 43 22 352. Non-magnetic lithium batteries or lead accumulators then take over the current supply of the amplifier unit.

The aforementioned accumulators or batteries are not mass produced. They are manufactured in single batches, or mass-produced batteries or accumulators are modified, e.g. in that electrodes are replaced. In each case, these specific accumulators or batteries are correspondingly expensive. Furthermore, the number of the charging and discharging cycles of the aforementioned accumulators is limited, requiring regular replacement. The charging process is comparatively slow and the actual energy content is unreliably known and is significantly dependent on age and prior usage. Furthermore, the disposal of accumulators or batteries in view of their heavy metal content is increasingly problematic.

A certain minimal energy density of an energy supply device is important for use with high-frequency reception antennas. An energy supply device having an energy density that is too low is not suitable for use with high-frequency reception antennas. The energy density of accumulators is not only adequate, but rather is so high that when the accumulator must be completely charged, this charging process takes a correspondingly long time. The use of conventional nickel-cadmium accumulators has the disadvantage that these have the known memory effect, i.e. they should be completely charged and completely discharged. The use in a "floating state" with repeated partial charging and discharging processes, as is typical during magnetic resonance tomography, is unfavorable for a conventional nickel-cadmium accumulator.

SUMMARY OF THE INVENTION

An object of the present invention is to provide a signal pickup or signal generator, especially a local high-frequency reception antenna, containing an energy supply device for use in or at a magnetic resonance tomography device wherein the aforesaid disadvantages can be avoided.

This object is inventively achieved in a signal transmitter and/or receiver (i.e., a signal interface) having an energy supply device formed by a double layer capacitor of high capacitance and high power density. Examples for double layer capacitors of high capacitance and high power density are products of Siemens Matsushita Components having the name UltraCap, that are described in more detail, e.g. in the article by C. Raible and H. Michel "UltraCap: Energy from Powerful Capacitors—Double Layer Opens New Dimensions", Components 6/98, pages 28 to 29. For use in or at a magnetic resonance tomography device, mass-produced products of these capacitors are suitable because these contain no ferromagnetic components. The charge condition can be clearly and simply ascertained on the basis of the output voltage of these capacitors. Their energy density is sufficiently high and attains nearly the energy density of conventional lead accumulators. They can be recharged at least 500,000 times. Their charging time is comparatively short and their weight comparatively low. Furthermore, these capacitors are ecologically unobjectionable because they contain no heavy metal constituents.

In an embodiment, the signal pickup or the signal generator has a charging coil for charging the energy supply device, this coil being able to derive the charging energy from gradient and/or high-frequency fields of the magnetic resonance tomography device. As a result, it is not required to remove these from the magnetic resonance tomography device for the purpose of the charging of signal pickup or signal generator. This form of the charging is especially expedient then because gradient fields are active during magnetic tomography an overwhelming majority of the time, and/or high-frequency pulses are emitted so that the charge energy is available at almost every point in time during the magnetic resonance examination. In a further embodiment, the charge condition is monitored using the output voltage of the double layer capacitor and a warning is given if warranted and/or an additional charging of the energy supply device is initiated via an appropriate control.

In another embodiment, the signal pickup or signal generator has a lead having at least one high ohmic conductor, preferentially a carbon fiber, for charging the energy supply device. As a result, charging is enabled with the energy source arranged outside of the magnetic resonance tomography device. This energy source can be, for example, the public electricity supply network. The high ohmic characteristic of the conductor, such as the use of a carbon fiber, prevents current levels from being reached which could induce currents that could be felt by a patient, particularly during magnetic resonance image scans wherein mechanical loops of the lead can form inside the magnetic resonance tomography device. Such induced currents can produce effects which are perceived as unpleasant by the examination subject or can even cause injuries to the examination subject.

In a further embodiment, the signal pickup or the signal generator has at least two terminal points that enable charging of the energy supply device outside of the magnetic resonance tomography device. As a result, convenient charging is enabled, e.g. using a charger cart.

In another embodiment, the signal pickup or signal generator has a communications device for communication with other devices. As a result, for example, signal forwarding to devices by a signal pickup operating in the magnetic resonance tomography device is enabled outside of the device in an online-operation. Equally as well, control of the signal pickup is possible in the reverse direction.

In a further embodiment, the aforementioned communications device is a microwave transmitting and/or receiving device and/or an infrared transmitting and/or receiving device. Both devices fulfill the requirement for a non-noise producing signal transmission in the hard electromagnetic environment of a magnetic resonance tomography device. The signal transmission is possible in principle in analog or digital implementation. The information content transmittable per time increment then depends on the available frequency bandwidth, or the baud rate. For optical signal transmission, commercial systems having bandwidths of up to approximately 10 MHZ are available. Signal transmission via microwaves allows still significantly higher bandwidths. Since the signal pickup or signal generator has its own energy supply device, a pre-processing and interim storage of data in the signal pickup or signal generator can be carried out given an inadequate transmission capacity.

In another embodiment, the signal pickup or signal generator has a light waveguide lead that is connected to the communications device. Noise-free signal transmission is assured in the electromagnetic environment of a magnetic resonance tomography device for this signal transmission path as well.

In a further embodiment, the signal pickup or signal generator is a local high-frequency reception antenna of a magnetic resonance tomography device. As described in detail initially, it is of a particular advantage to implement such an antenna without a lead. The use of a communications device with such a leadless high-frequency reception antenna is of special importance because the magnetic resonance signals received by the antenna have a high information content and are to be transmitted to devices for further processing within the shortest time. Furthermore, the local high-frequency reception antenna is to be tuned by control during the transmitting mode of other high-frequency antennas for the triggering of magnetic resonance signals, such that no impermissibly high power densities occur which can endanger the examination subject.

In another embodiment, the signal pickup receives medical-diagnostic parameters of a live examination subject, especially body temperature, ECG-signals, blood pressure, respiratory movements, etc. As a result, for example, the monitoring of unstable patients can be done during a magnetic resonance tomography scan.

In another embodiment, the signal generator produces sensory stimuli for a live examination subject, particularly acoustical, optical, electrical stimuli, etc. In one embodiment, the signal generator is fashioned, for example as a hearing aid which supplies specific sounds, tone sequences or music to a patient during a functional magnetic resonance tomography.

DESCRIPTION OF THE PREFERRED EMBODIMENTS

Figure 1:
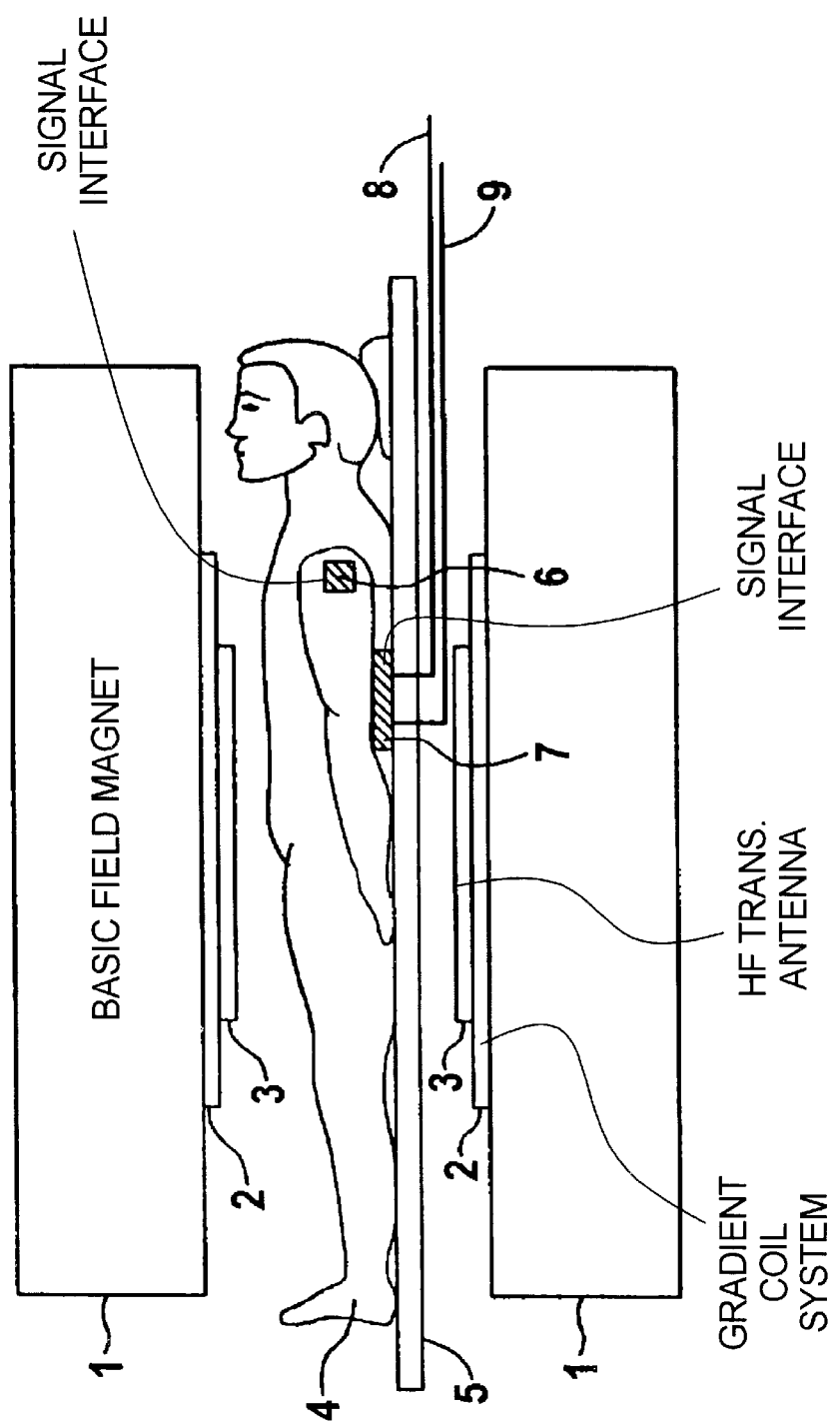
FIG. 1 is a sectional view of a magnetic resonance tomography device having a signal pickup or signal generator with no lead as well as with a lead.

FIG. 1 shows a sectional view through a magnetic resonance tomography device in one embodiment of the invention. Only the basic components of the device are represented here: a basic field magnet 1, a gradient coil system 2, a high-frequency transmitting antenna 3 as well as a patient 4 on a patient examination table 5. Furthermore, a lead-less signal pickup or generator (signal interface) 6 as well as a signal pickup or generator 7 (signal interface) with a lead are shown. The signal pickup or generator 7 has at its disposal two leads 8 and 9. The lead 8 then serves for charging an energy supply device 10 in the signal pickup or generator 7. The lead 9 is connected to a communications device 12 of the signal pickup or generator 7 and serves for signal transmission. The signal pickup or generator 6 serves, for example, for acquiring the temperature of the patient 4 and is therefore attached to the skin of the patient 4. The signal pickup or generator 7 is, for example, a local high-frequency reception antenna.

Figure 2:
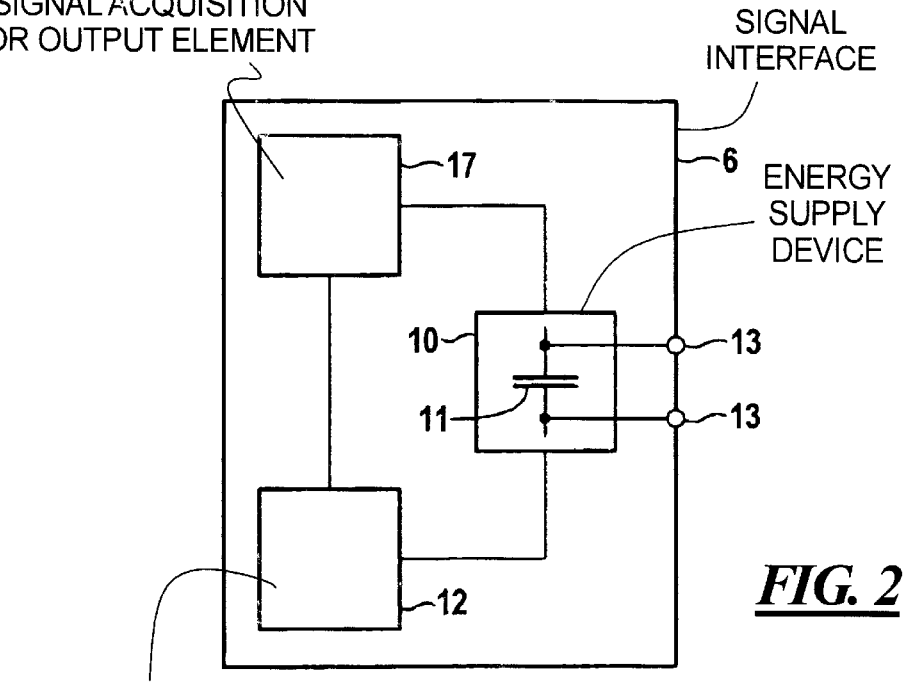
FIG. 2 is a detailed illustration of a lead-less signal pickup or signal generator in accordance with the invention, in a first embodiment.

FIG. 2 shows the lead-less signal pickup or generator 6 in a first embodiment in detail. The signal pickup or generator 6 has a signal pickup element or signal output element 17, a communications device 12 as well as an energy supply device 10 that contains a double layer capacitor 11. The energy supply device 10 is connected for the energy supply of the signal pickup element or signal output element 17 as well as the communications device 12. Furthermore, the element 17 is connected to the device 12 for information and data exchange. The signal pickup or generator 6 has two terminal points 13 via which charging of the double layer capacitor 11, e.g. using a charging cart, can take place.

Figure 3:
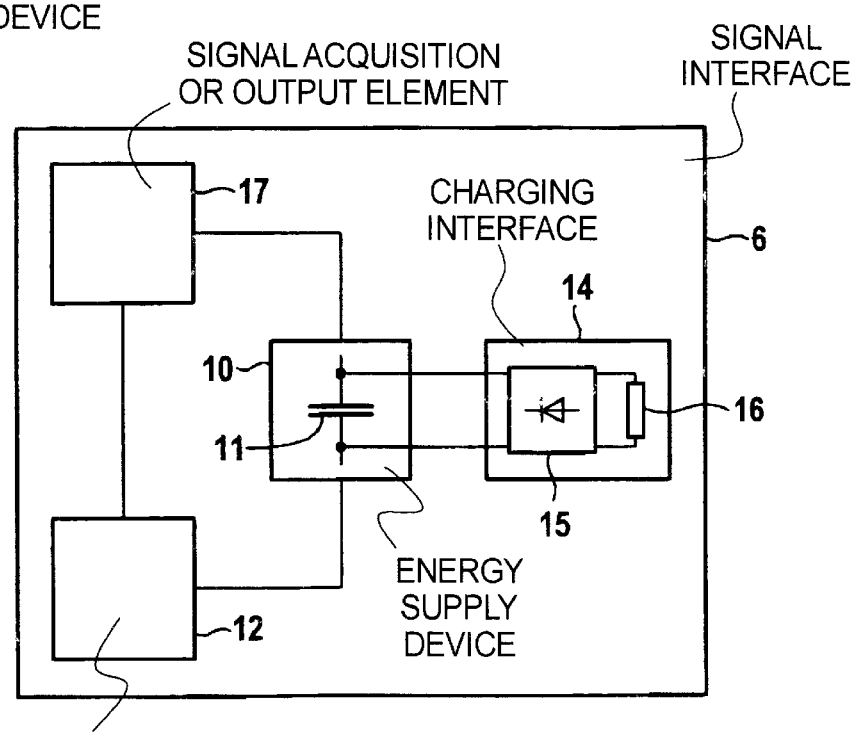
FIG. 3 is a detailed illustration of a lead-less signal pickup or signal generator in accordance with the invention, in a second embodiment.

FIG. 3 shows the lead-less signal pickup or generator 6 in a second embodiment in detail. Compared to FIG. 2, the signal pickup or generator 6 in FIG. 3 exhibits no terminal points 13, but rather contains a charging device 14 formed by a rectifier component 15 and a charging coil 16. With the charging coil 16, energy is correspondingly derived from the gradient fields and/or high-frequency fields of the magnetic resonance tomography device for charging the double layer capacitor 11 and is fed to the double layer capacitor 11.

Figure 4:
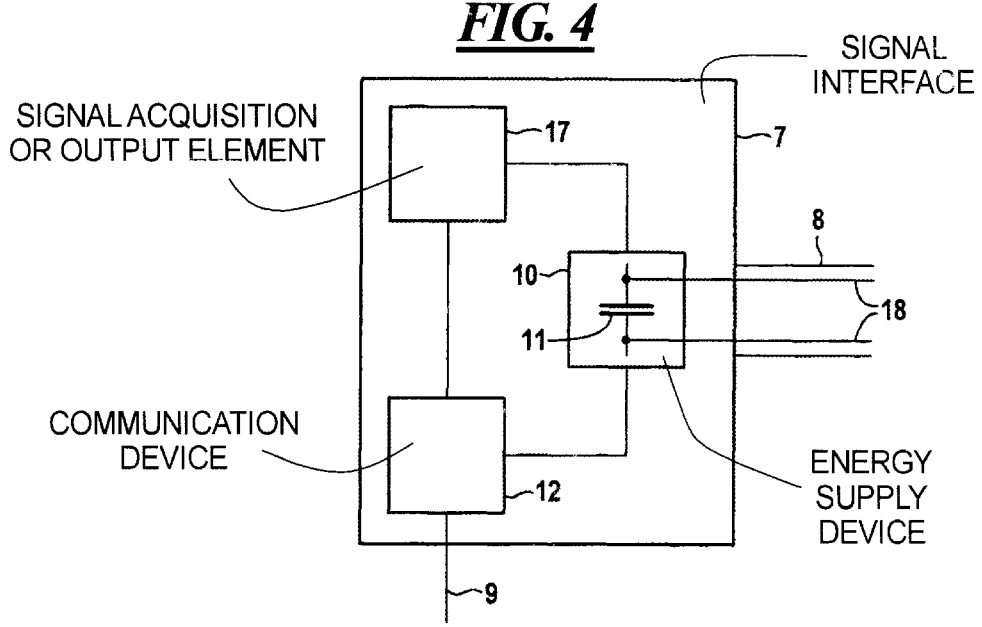
FIG. 4 is a detailed illustration of a signal pickup or signal generator with a lead, in accordance with the invention.

FIG. 4 shows the signal pickup or generator 7 with a lead in detail. Compared to the signal pickup or generator 6 of FIG. 2, the signal pickup or generator 7 from FIG. 4 has no terminal points 13, instead there are, for example two carbon fibers 18 within the lead 8 connected in such a manner to the energy supply device 10, or to the double layer capacitor 11, so that charging of the double layer capacitor 11 with an energy source outside of the magnetic resonance tomography device is possible at any time. In addition, the lead 9 of the signal pickup or generator 7 is in this embodiment is a light waveguide that is connected at the communications device 12 and serves the data exchange with other devices, for example, electronic further processing devices.

Figure 5A:
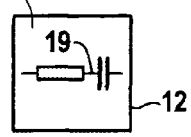
FIGS. 5A and 5B are respective schematic illustrations of two embodiments of a communications device for an inventive signal pickup or signal generator.
Figure 5B:
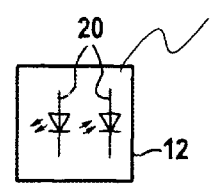

FIGS. 5A and 5B show two embodiments of the communications device 12 in schematic illustrations. In the embodiment of FIG. 5A, the communications device 12 contains a microwave transmitting and receiving device 19 and in the embodiment of FIG. 5B, the communications device 12 contains an optical transmitting and receiving device, for example, in an infrared transmitting and receiving device 20.

Figure 6A:
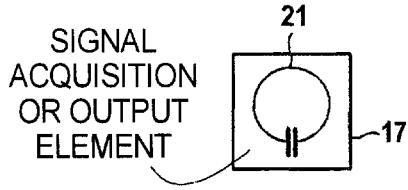
FIGS. 6A an 6B are respective schematic illustrations of two embodiments of a signal pickup element of a signal pickup in accordance with the invention.
Figure 6B:
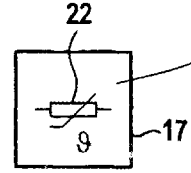

FIGS. 6A and 6B show two embodiments of the signal pickup element 17 in a schematic illustrations. In the embodiment of FIG. 6A, the signal pickup element 17 contains a high-frequency reception element 19 so that the signal pickup 7 forms a local high-frequency reception antenna of a magnetic resonance tomography device. In the embodiment of FIG. 6B, the signal pickup element 17 of the signal pickup 6 contains, for example, a thermoelement 22, with which, for example, the body temperature of a patient is acquired during a magnetic resonance examination.

Figures 7A, 7B:
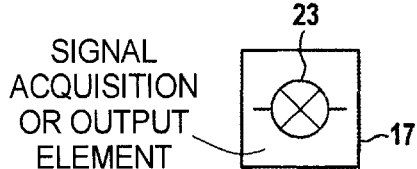
FIGS. 7A, 7B and 7C are respective schematic illustrations of three embodiments of a signal output element of a signal generator in accordance with the invention.
Figure 7C:
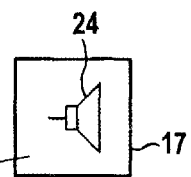

FIGS. 7A, 7B and 7C show three embodiments of the signal output element 17 in schematic illustrations. The signal output element 17 in the embodiment of FIG. 7A contains, for example, a simple lamp 23 for producing optical sensory stimuli. In the embodiment of FIG. 7B, the signal output element 17 contains a speaker 24 for producing acoustic sensory stimuli and in the embodiment of FIG. 7C, there is a stimulus-current production device 25 for producing electrical stimuli.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance apparatus comprising:

a magnetic resonance scanner, adapted to receive an examination subject therein, for obtaining magnetic resonance data from said examination subject; and a signal interface comprising an interface element adapted for interaction with said examination subject while said examination subject is in said magnetic resonance scanner; and an energy supply device connected to said interface element and comprising a double layer capacitor of high capacitance and high power density.

2. A magnetic resonance apparatus as claimed in claim 1 further comprising a charging coil for charging said energy supply device, said charging coil deriving charging energy from electromagnetic fields in said magnetic resonance scanner.

3. A magnetic resonance apparatus as claimed in claim 1 comprising a lead having at least one high ohmic conductor for charging said energy supply device.

4. A magnetic resonance apparatus as claimed in claim 3 wherein said high ohmic conductor is a carbon fiber conductor.

5. A magnetic resonance apparatus as claimed in claim 1 comprising at least two terminal points adapted for charging said energy supply device from a location outside of said magnetic resonance tomography apparatus.

6. A magnetic resonance apparatus as claimed in claim 1 wherein said magnetic resonance scanner contains a plurality of apparatus components, and wherein said signal interface comprises a communications device, connected to said energy supply device, for communicating with at least one of said components.

7. A magnetic resonance apparatus as claimed in claim 6 wherein said communications device is selected from the group consisting of a microwave transmitting device and a microwave receiving device.

8. A magnetic resonance apparatus as claimed in claim 6 wherein said communication device is selected from the group consisting of an infrared transmitting device and an infrared receiving device.

9. A magnetic resonance apparatus as claimed in claim 6 further comprising a light waveguide connecting said communications device to said at least one component.

10. A magnetic resonance apparatus as claimed in claim 1 wherein said interface element is a high-frequency reception antenna for nuclear magnetic resonance signals.

11. A signal interface as claimed in claim 1 wherein said interface element is a physiological signal pick-up for obtaining physiological signals selected from the group consisting of body temperature, ECG signals, blood pressure and respiratory movements.

12. A signal interface as claimed in claim 1 wherein said interface element is a sensory stimuli emitter adapted to stimulate said examination subject.

13. A magnetic resonance apparatus as claimed in claim 12 wherein said emitter is selected from the group consisting of acoustic emitters, optical emitters and electrical stimulus emitters.

\* \* \* \* \*